(12) United States Patent
Chirovsky et al.

(10) Patent No.: US 9,322,262 B2
(45) Date of Patent: Apr. 26, 2016

(54) PULSED NEUTRON GENERATOR TUBE DESIGN WHICH EXTENDS THE LIFETIME OF A CATHODE

(71) Applicant: Schlumberger Technology Corporation, Sugar Land, TX (US)

(72) Inventors: Leo Chirovsky, East Windsor, NJ (US); Luke Perkins, Plainsboro, NJ (US); Jani Reijonen, Princeton, NJ (US); Loic Vilde, New Brunswick, NJ (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 571 days.

(21) Appl. No.: 13/718,888

(22) Filed: Dec. 18, 2012

(65) Prior Publication Data

US 2013/0180780 A1    Jul. 18, 2013

Related U.S. Application Data

(60) Provisional application No. 61/578,963, filed on Dec. 22, 2011.

(51) Int. Cl.
| | | |
|---|---|---|
| *G01N 23/00* | (2006.01) | |
| *H05H 3/06* | (2006.01) | |
| *E21B 47/00* | (2012.01) | |
| *G01N 33/24* | (2006.01) | |
| *G21G 4/02* | (2006.01) | |

(52) U.S. Cl.
CPC .............. *E21B 47/00* (2013.01); *G01N 23/005* (2013.01); *G01N 33/24* (2013.01); *G21G 4/02* (2013.01); *H05H 3/06* (2013.01)

(58) Field of Classification Search
CPC ............ E21B 47/00; H05H 3/06; G01V 5/10; G21G 4/02; G01N 23/005; H01J 27/02; H01J 37/08; H01J 3/04
See application file for complete search history.

(56) References Cited

U.S. PATENT DOCUMENTS

| | | | | |
|---|---|---|---|---|
| 3,309,522 | A * | 3/1967 | Youmans et al. | 376/111 |
| 4,432,929 | A * | 2/1984 | Bridges | 376/119 |
| 5,293,410 | A | 3/1994 | Chen et al. | |
| 5,699,246 | A | 12/1997 | Plasek et al. | |
| 8,822,912 | B2 * | 9/2014 | Reijonen et al. | 250/253 |
| 8,866,068 | B2 * | 10/2014 | Reijonen et al. | 250/256 |
| 9,052,405 | B2 * | 6/2015 | Zhou et al. | |

(Continued)

FOREIGN PATENT DOCUMENTS

WO        2010090795 A1    8/2010

OTHER PUBLICATIONS

European Search Report issued in EP application 12861003.7 on Jul. 7, 2015, 3 pages.

(Continued)

*Primary Examiner* — Daniel P Stephenson
(74) *Attorney, Agent, or Firm* — Michael Dae (57) ABSTRACT

A method for operating a pulsed neutron generator including an ionizer with an electron emitting cathode and a grid wherein the cathode and grid are disposed in a sealed chamber. At least one of the following is applicable to the ionizer; a distance between the cathode and the grid, a cathode current and/or a potential on the grid are selected such that the ionizer operates at most about one-half the space charge limited current for a grid current selected to provide a predetermined amount of neutron production.

18 Claims, 8 Drawing Sheets

(56) References Cited

U.S. PATENT DOCUMENTS

| | | |
|---|---|---|
| 2009/0146052 A1 | 6/2009 | Groves et al. |
| 2009/0219028 A1 | 9/2009 | Perkins et al. |
| 2010/0237874 A1 | 9/2010 | Yang et al. |
| 2011/0049345 A1* | 3/2011 | Roberts ............... 250/269.6 |
| 2011/0180698 A1 | 7/2011 | Stephenson |
| 2013/0170592 A1* | 7/2013 | Zhou et al. ............... 376/114 |
| 2013/0180780 A1* | 7/2013 | Chirovsky et al. .......... 175/50 |
| 2013/0256522 A1* | 10/2013 | Perkins et al. ............ 250/259 |
| 2014/0086376 A1* | 3/2014 | Perkins ..................... 376/114 |
| 2014/0117246 A1* | 5/2014 | Zhou et al. ............... 250/375 |

OTHER PUBLICATIONS

Office Action issued in EP application 12861003.7 on Jul. 30, 2015, 6 pages.

* cited by examiner

PULSED NEUTRON GENERATOR TUBE DESIGN WHICH EXTENDS THE LIFETIME OF A CATHODE

CROSS-REFERENCE TO RELATED APPLICATIONS

Priority is claimed from U.S. Provisional Application No. 61/578,963 filed on Dec. 22, 2011.

STATEMENT REGARDING FEDERALLY SPONSORED RESEARCH OR DEVELOPMENT

Not applicable.

BACKGROUND

This disclosure relates generally to the field of electrically operated "pulsed" neutron sources or "generators" used for evaluating neutron interaction properties of subsurface formations from within wellbores. More specifically, the disclosure relates to structures and operating methods for such pulsed neutron generators in which a heated electron emitting ("dispenser") cathode may have longer lifetime than such pulsed neutron generators known in the art that use cathodes sensitive to degradation, such as dispenser cathodes. or cold cathodes, such as nanotipped emitters.

Pulsed neutron generators (PNGs) are known in the art for use in wellbore formation evaluation ("logging") tools for evaluating neutron interaction properties of formations penetrated by a wellbore. Porosity, salinity, formation density, hydrogen content, formation elemental fractions, etc., can all be determined by measurements of interaction products of high energy neutrons from a PNG with such formations. Such well logging tools may include a sealed, hydrogen isotope fusion reaction tube to generate controlled duration pulses or "bursts" of neutrons at a specific energy level (usually 14 million electron volts—"MeV" for, example, for a deuterium-tritium fusion reaction). An important component of a PNG is an ion generator ("ionizer") disposed within the sealed fusion reaction tube that generates hydrogen isotope ions. The hydrogen isotope ions are accelerated in an accelerator section of the sealed fusion reaction tube to produce nuclear fusion reactions in a metal-hydride target containing high concentrations of adsorbed hydrogen isotope atoms. The ions are generated in the ion generator by causing a molecule or atom of gas to be impacted by a sufficiently energetic electron and thereby stripping a bound electron from the molecule or atom. The energy of the incident (impacting) electron can vary from a few tens of electron volts (eV) to a few hundred eV. In "hot" cathode-based neutron tubes, the electrons are produced by a thermionic material(s), e.g., barium oxide, strontium oxide and calcium oxide imbedded onto an electrically heated cathode body. Such type of cathode is typically biased at or near (e.g., within a few volts) ground potential. Such cathode material needs to be heated to high temperature, typically about 1000° C., and a suitable electric field needs to be applied proximate the surface of the cathode material to extract and accelerate/energize the thermionic electrons. Such cathodes are referred to as "dispenser" cathodes. A dispenser cathode emits more electrons as its temperature rises, but in order to provide sufficient ionization energy to the thermionic electrons emitted from the cathode, a high transmissivity (at least 75%) grid or an electrode may be positioned near the face of the cathode and is biased positive at a potential with reference to the cathode from a few tens to a few hundreds of volts (the grid voltage referred herein as $V_{grid}$). Eventually the grid, and/or other metal surfaces biased to $V_{grid}$, collect emitted electrons, constituting a grid current, referred to herein as $I_{grid}$. The cathode temperature, and corresponding electron emission rate, may be controlled such that $I_{grid}$ reaches a value that causes sufficient ion formation for desired neutron production In order to maintain a stable neutron output, several voltage and/or current control loops may be used in connection with a typical neutron tube. One of these control loops maintains a constant $I_{grid}$ at a constant $V_{grid}$ by adjusting the cathode heater current ($I_{cat}$), and thereby the cathode temperature, via a negative feedback loop; that is, if $I_{grid}$ rises above a set point then $I_{cat}$ is lowered (so that thermionic electron emission is correspondingly reduced by reduction in cathode temperature); conversely, if $I_{grid}$ falls below its set point then $I_{cat}$ is raised to that $I_{grid}$ increases to the set point.

Over time, as the neutron tube is used, the cathode may begin to degrade. As a result, $I_{cat}$ (and the corresponding cathode temperature) needs to be gradually increased to maintain the set point $I_{grid}$. The lifetime of dispenser cathodes is nominally rated to be over 10,000 hours by their manufacturers, but such lifetime rating is relevant only when the cathode is operated in a high quality vacuum. For neutron tubes used in well logging instruments, however, some cathodes have been known to last only a few hundred hours. Even if such degraded cathodes can still emit electrons, their end of life is generally defined as the point in time when the cathode can no longer maintain a selected $I_{grid}$ at a maximum acceptable $I_{cat}$, such maximum current being related, for example, to available power to operate the cathode and self-destructive limits on the cathode current.

Figure 1:
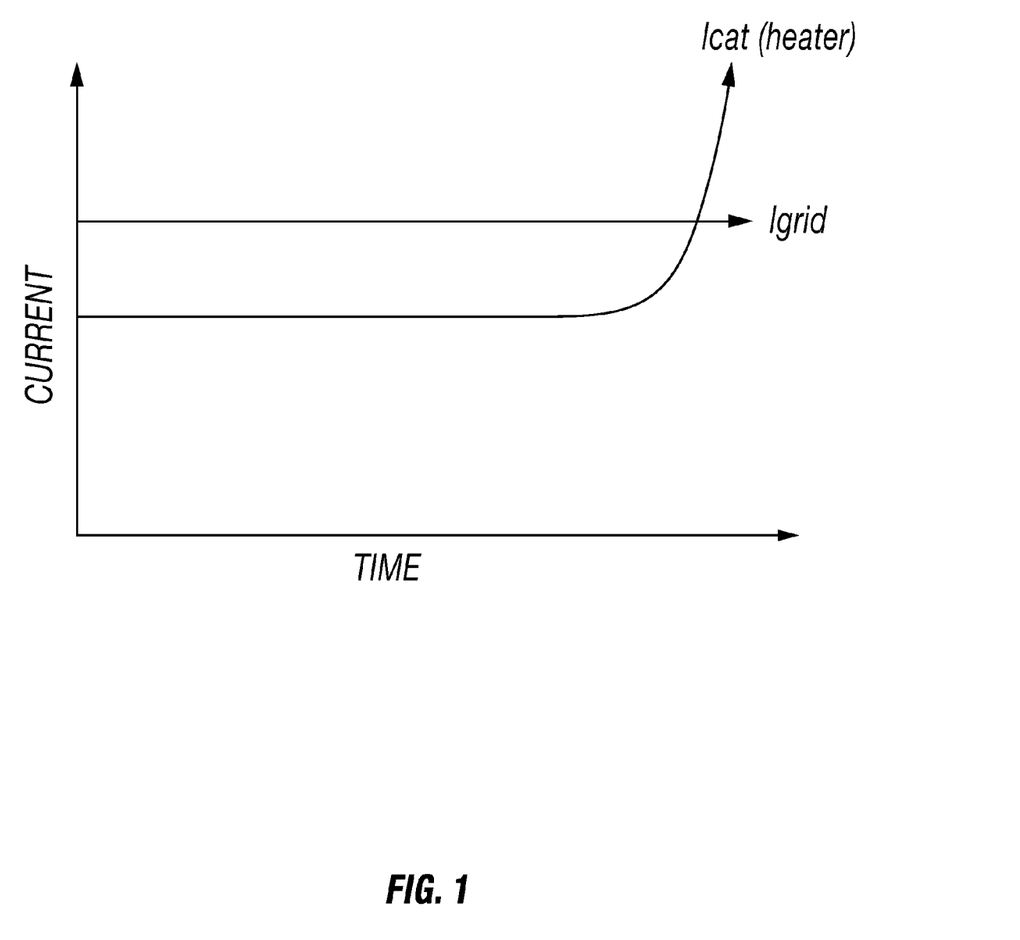
FIG. 1 is a graph showing the temporal evolution operating parameters of a pulsed neutron generator (PNG) known in the art.

Neutron tube dispenser cathode failures were reproduced in the laboratory, while operating parameters were recorded in order to establish how cathode degradation over time proceeds to eventual cathode failure. FIG. 1 shows an example of cathode current needed to maintain a selected setpoint grid current with respect to time. As shown in FIG. 1, neutron tube dispenser (hot) cathode degradation may be characterized, with reference to the cathode current, $I_{cat}$, as gradual at first, but then suddenly becomes very rapid. The time at which the rapid degradation and ultimate cathode failure takes place in neutron generators is substantially shorter than advertised/ expected lifetimes of commercially available cathodes, and more significantly, the rapid degradation may take place at unpredictable times.

What is needed is a neutron tube structure and operating technique that can reduce the effects of sudden cathode degradation in order to extend the useful lifetime thereof.

SUMMARY

One aspect of the disclosure is a pulsed neutron generator. A pulsed neutron generator according to the present aspect includes an ionizer including an electron emitting cathode and a grid. The cathode and grid are disposed in a sealed chamber. A distance between the cathode and the grid, a cathode electron emissions rate and/or a potential impressed on the grid are selected such that the ion generator operates at most about one-half the space charge limited current for a grid current selected to provide a predetermined amount of neutron production.

Other aspects and advantages will be apparent from the description and claims which follow.

DETAILED DESCRIPTION

Figure 2:
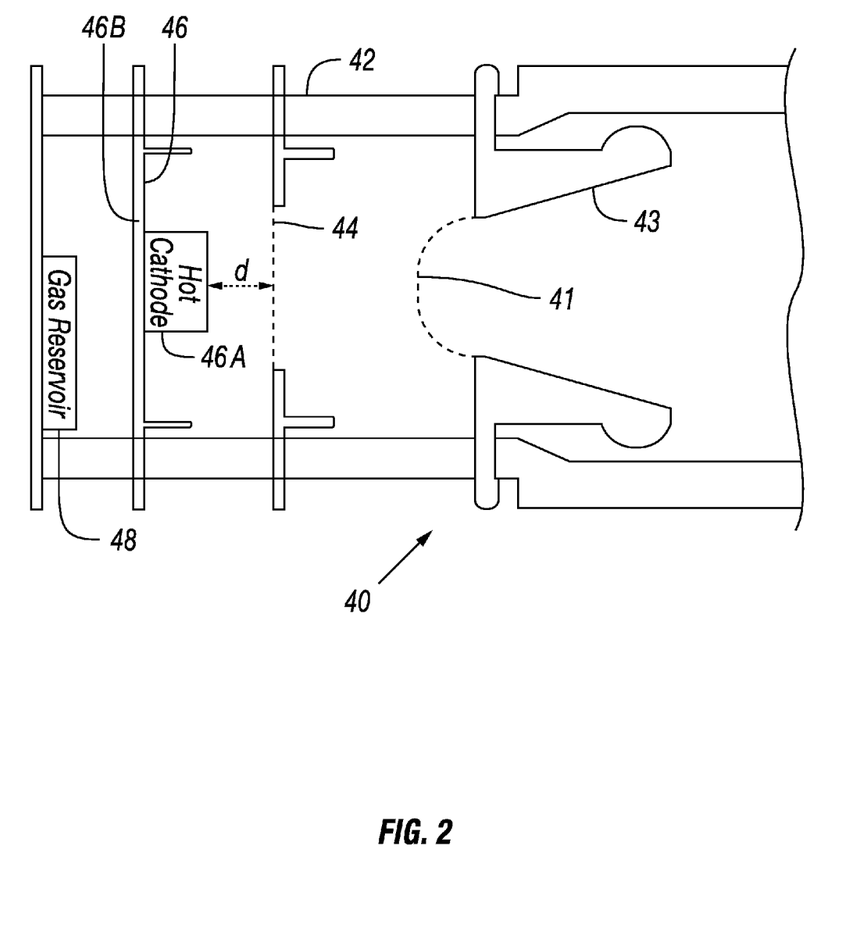
FIG. 2 shows an example ionizer.

FIG. 2 shows an example ionizer 40 from a neutron generator tube. A gas reservoir 48 may be made from a material having adsorbed therein hydrogen isotopes such that heating the gas reservoir 48 to a selected temperature will result in a selected pressure of hydrogen isotope gas inside the sealed neutron generator tube. A chamber in which the ionizer 48 components are sealed, as well as other components of the neutron generator tube are omitted from FIG. 2 for clarity of the illustration. A cathode assembly 46 including a heated dispenser cathode 46A is shown mounted spaced apart be a small distance from a ceramic support 46B in the sealed tube 42 at a selected position which may be proximate the gas reservoir 48. A grid 44 as explained in the Background section herein may be disposed proximate the cathode 46 at a selected distance "d," which will be further explained below. Although a grid is shown in FIG. 2, as explained in the background section, a simple electrode may be used in other examples. For purposes of defining the scope of the present disclosure, the term "grid" may be used to mean either an actual grid or an electrode; both may be considered to operate with equal effect as it concerns the present disclosure. An extractor 43 may be disposed proximate the longitudinal end of the ionizer 48. In some examples a dome screen 41 may be included with the extractor 43. Circuits to supply the necessary current to operate the foregoing components may be similar to those described, for example, in U.S. Pat. No. 5,293,410 issued to Chen et al. and incorporated herein by reference. FIG. 2 is a schematic drawing and certain mounting features, electrical feedthroughs and connecting wires for power and signals to the cathode 46A, extractor 43, gas reservoir 48 and grid or electrode 44 are not shown in FIG. 2 for simplicity of the illustration but will be appreciated by those skilled in the art as being present in any example neutron tube.

Figure 3:
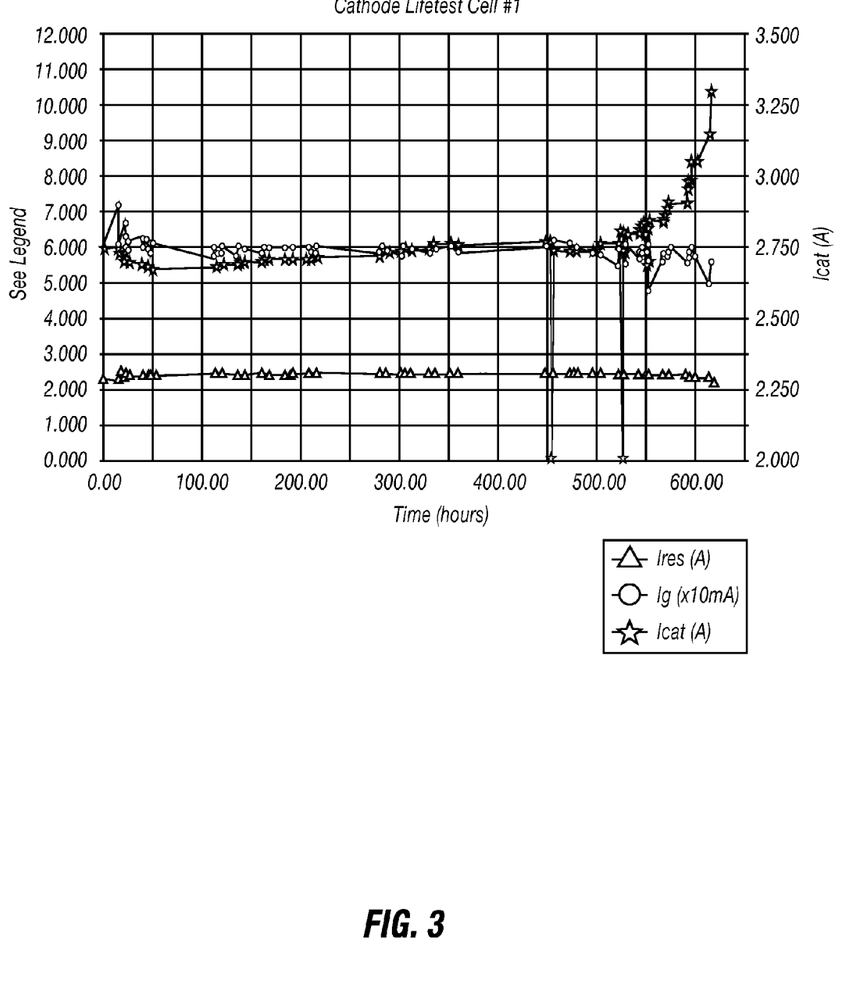
FIG. 3 shows plots of results for cumulative runs of a cathode test cell in which the cathode failed.

FIG. 3 shows graphs of test results using an ionizer as part of a neutron generator tube such as one described, for example, in U.S. Pat. No. 5,293,410 issued to Chen et al. The $I_{grid}$ selected to be maintained during the test was 60 milliamperes (mA) peak, with a 12 milliampere average current (formed by a cycle consisting of 20 μs grid current on/ 80 μs grid current off; other cycles may be used in actual well logging operations depending on the type of measurement being made). The test used a sealed chamber configured, again, as may be described in the Chen et al. '410 patent. Very gradual cathode degradation began and continued for approximately 390 operating hours. Afterward, the cathode degradation rate increased as may be indicated by increasing cathode current thereafter. Finally, the cathode degraded very rapidly and failure occurred after only about 70 additional operating hours as shown by the cathode current. Just as in the neutron tube case described in the Background section herein with reference to FIG. 1, the cathode degradation was gradual at first, but then abruptly became very rapid, as if caused by depletion or poisoning effects. The gradual degradation illustrated FIG. 3 is believed to be due to several effects. The first, and believed to be the dominant effect, is contamination. It is well known in the art that a dispenser cathode are highly susceptible to become contaminated ("poisoned") in the presence of various elements in the atmosphere present in a neutron tube. However, hydrogen ions emitted from the ionizer impact many surfaces in the neutron tube, which can then sputter the different materials forming or embedded in the various components in the neutron tube, including trace amounts of impurities. Many of such impurities may be harmful to the dispenser cathode. Contamination rates can vary to a great extent as a result of many difficult to control parameters.

A second possible, potentially further deleterious effect on cathode degradation is a change in heat dissipation rate. As neutron tubes age, often the gas pressure must be raised to maintain a constant ion beam current. The gas atmosphere in the neutron tube dissipates some heat from the cathode. Therefore, higher cathode current may be required to maintain the same cathode temperature in the higher pressure gas atmosphere so that the same electron emission rate can be maintained. Whatever the specific cause, each of the foregoing causes of degradation may not be easily controlled below a certain threshold and so may always be present in any neutron tube to some degree. Fortunately, the gradual degradation causes may operate slowly enough to give the cathode greater longevity as long as the previously described rapid degradation causes do not begin.

The eventual rapidly accelerating degradation observed in FIG. 3 at first appeared to have been due to a sudden dominance of any one or more of the above-described gradual degradation mechanisms.

Figure 4:
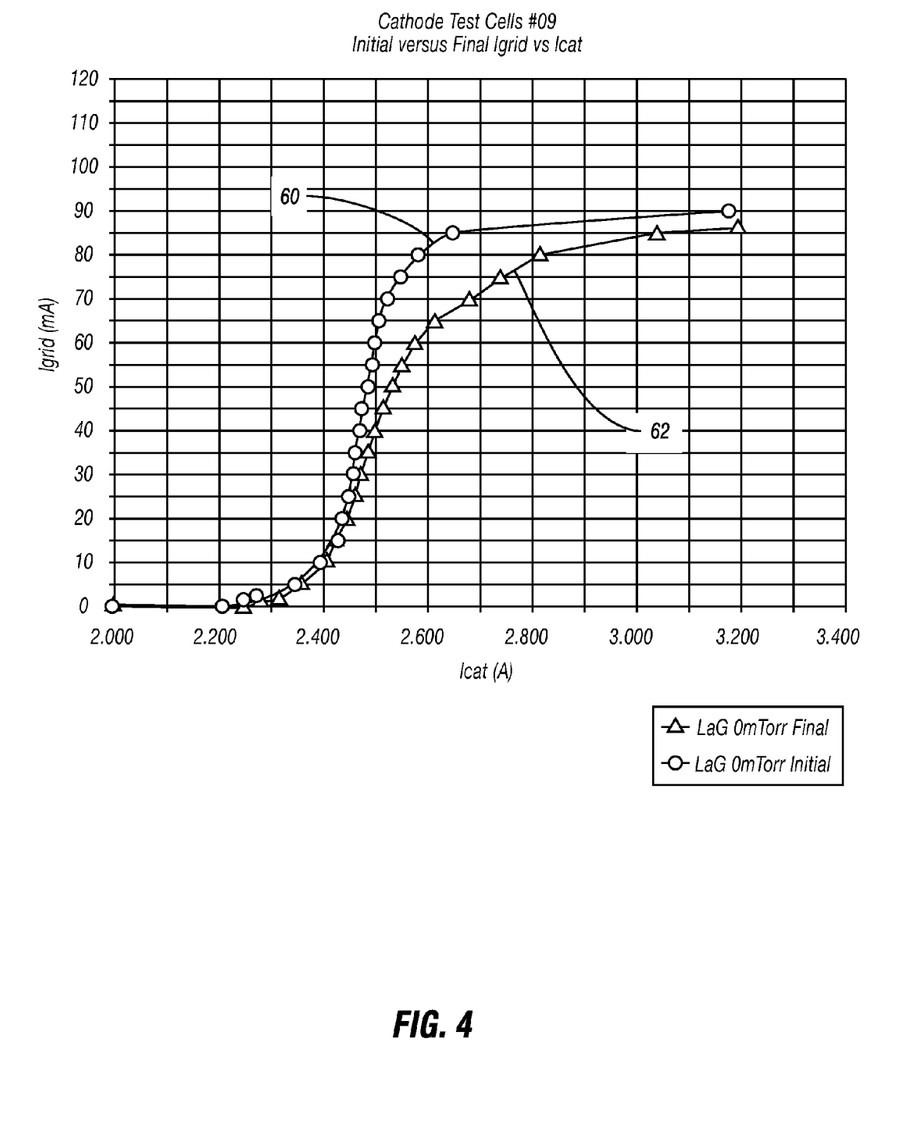
FIG. 4 shows plots comparing the cathode current with respect to the grid current characteristics of a cathode before and after an extended duration operating test.

In the experiments explained with reference to FIG. 3, cathodes were carefully characterized, wherein the dependence of $I_{grid}$ with respect to $I_{cat}$ was determined under various conditions over a wide range of values. The results of such experiments showed that the cathodes were being operated close to the space charge limit for the region of the neutron tube interior for the given cathode-grid spacing ("d" in FIG. 2). The gradual degradation may drive the cathode and grid closer to the space charge limit over time, whereupon an increase in cathode current no longer increases electron emission from the cathode as expected. An example of the foregoing is shown in FIG. 4, which is a graph of grid current as a function of cathode current at the beginning of the test (curve 60) and at the end of the test (curve 62). The space charge phenomenon may cause a pulsed neutron tool's neutron tube current and/or voltage control loops to drive $I_{cat}$ to its maximum allowed limit. Child's Law shows that in the cathode/grid plane-parallel diode configuration, the space-charge limited grid current is given by the equation shown below.

$$I_{grid} = JS = \frac{4\varepsilon_0 \sqrt{(2e/m_e)}(S)(V_{grid})^{3/2}}{9d^2} \quad \text{(Eq. 1)}$$

where $V_{grid}$ is the grid voltage, $I_{grid}$ is the grid current, J is the current density, S is the cathode electron emitting surface area normalized for the emissivity per unit area, and d is the length of the cathode/grid gap. $\epsilon_0$ is the dielectric permittivity of free space (vacuum), e and $m_e$ are the unit charge and mass of an electron, respectively. $I_{grid}$ may be selected to provide a selected or predetermined amount of neutron production within the neutron generator tube. Note that S may depend on the material used for the cathode (i.e., its specific electron emissivity per unit surface area), and in the case of dispenser type cathodes on the temperature of the cathode emitting surface. While the foregoing example is for a heated (dispenser) type cathode, it is believed the principle of operation according to the present disclosure is applicable to unheated cathodes as well.

Figure 5:
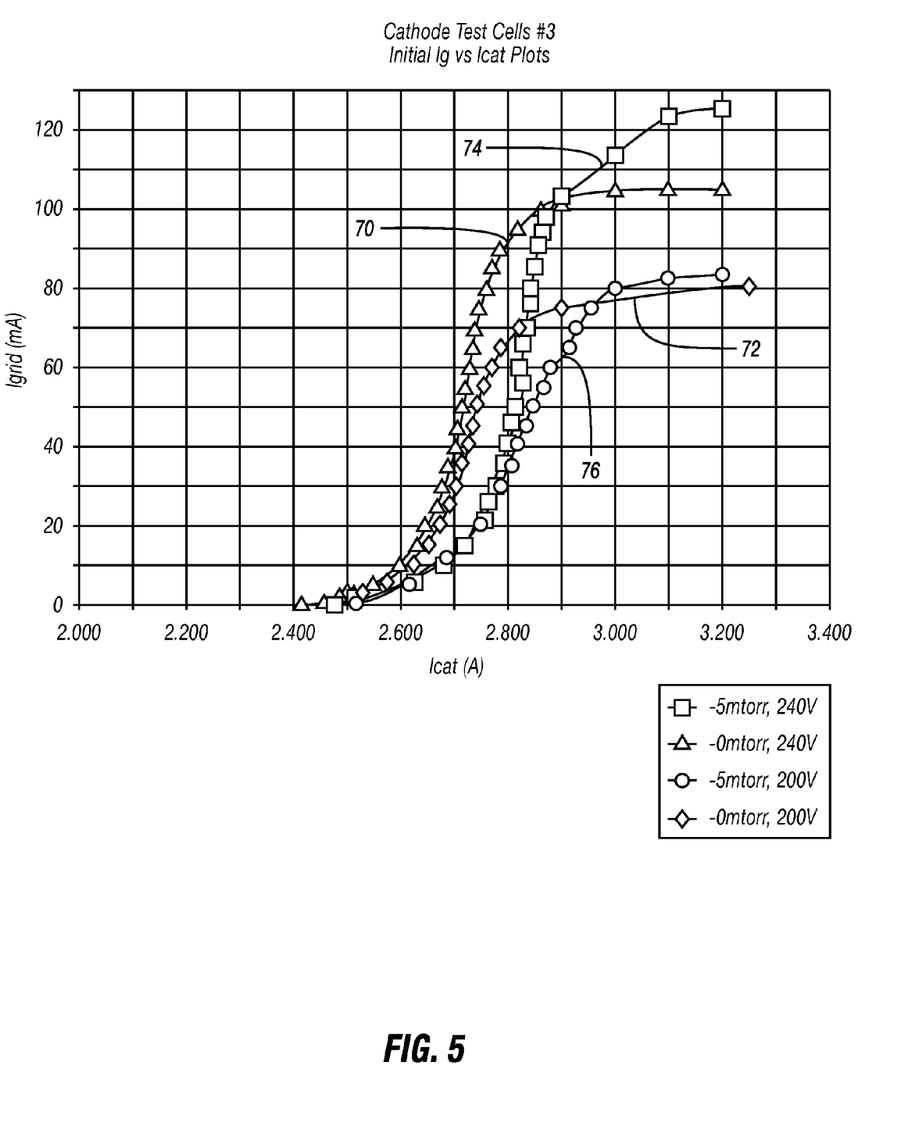
FIG. 5 shows a plot comparing initial cathode current with respect to the grid current of a cathode design known in the art with $V_{grid}$ at 200 V and at 240 V.

One way to increase the $I_{grid}$ limit is to increase the cathode electron emitting area S. In the necessarily limited space of the interior of a neutron tube used for well-logging, and within the necessary power limitations on heat dissipation in a dispenser cathode, S, however, is already substantially as large as it can be in a practical pulsed neutron well logging instruments known in the art, such area being less than about 12 square millimeters (mm$^2$). Another approach to increase the $I_{grid}$ limit is to increase $V_{grid}$, however, $V_{grid}$ is already near its practical maximum in pulsed neutron instruments known in the art; increasing $V_{grid}$ may therefore increase undesirable power dissipation (the power dissipation being equal to $I_{grid} \times V_{grid}$) in the ion generator, and may be impracticable because of space and available power limitations of a practical pulsed neutron well logging instrument as well as having possible reliability implication. Examples of the foregoing are shown in FIG. 5, which shows graphs of grid current as a function of cathode current at the beginning of the test in a vacuum, at curves 70 and 72, respectively, and in a hydrogen isotope atmosphere at curves 74 and 76, respectively. Additionally, $V_{grid}$ only improves $I_{grid}$ by its three halves power ($V_{grid}^{(3/2)}$).

Figure 6:
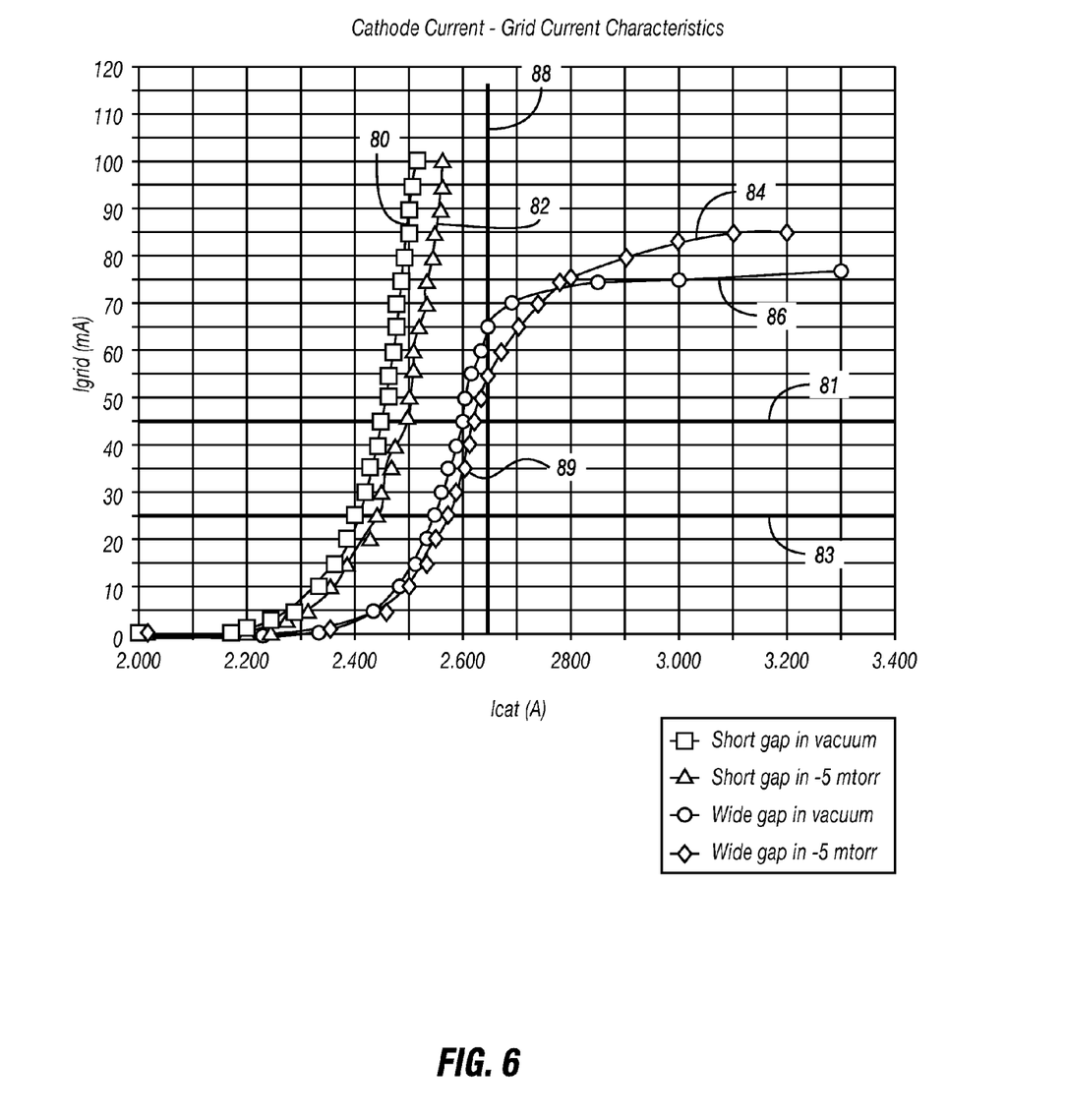
FIG. 6 shows a plot comparing the cathode current with respect to the grid current of a neutron tube with a short gap (one embodiment of the new proposed design) and a wide gap (prior art design) between the cathode and the grid at a $V_{grid}$ of 200 V.

One example way to increase $I_{grid}$ may be to decrease the cathode/grid spacing, "d." In the present example, "d" was decreased from 0.055 inches (in the above described neutron generator of the Chen '410 patent) to 0.025 inches. FIG. 6 shows how well this second approach may work, wherein the smaller gap grid current as a function of cathode current is shown in a vacuum and in a 5 mtorr atmosphere of hydrogen isotopes at curves 80 and 82, respectively. Corresponding response using the original, wider gap is shown at curves 84 and 86, respectively. In addition, the foregoing configuration may also allow a decrease in $V_{grid}$ so as to allow neutron tube operation with lower heat dissipation at/on the grid. As may be observed in FIG. 6, by reducing the spacing, "d," the cathode can also sustain a given $I_{grid}$ while operating at a lower $I_{cat}$ (and thus at a lower temperature) which can then decrease the gradual degradation rate. In the foregoing example, the $V_{grid}$ may be reduced from a range of about 180 to 240 volts to a range of about 100 to 180 volts, nominally less than 200 volts, and the cathode emitting area is less than about 0.12 mm$^2$.

Thus it is believed that a longer lifetime for a heated dispenser cathode in a neutron tube may be obtained if for a selected cathode electron emission rate the spacing between the cathode and the grid is reduced, or if $V_{grid}$ is increased to a practical maximum depending on the available electrical power, insulating properties of the materials used in the neutron generator tube and the available space within the well logging instrument for the neutron generator tube. A number of neutron generator tubes have been made according to the foregoing example embodiment (i.e., cathode to grid spacing of 0.025 inches) with a grid voltage correspondingly reduced to 100 to 180 volts, and none of the tested neutron generator tubes have had cathode failures or even showed substantial cathode degradation even after operation times substantially beyond those experienced using neutron generator tubes made and operated according to techniques known in the art.

Still referring to FIG. 6, the graph of grid current with respect to cathode current has a boundary 88 above which the grid current is limited by the space charge effect. Below the boundary 88, the grid current may be affected/limited by the cathode current and corresponding thermionic electron emission rate from the cathode. In the present example, a cathode current which results in the ionizer operating at 50% of the space charge limit is shown at 89. Cathode current (and the corresponding electron emission rate) and corresponding grid voltage to result in the displayed grid currents may be operated within a selected range of one half the space charge limit, e.g., within 20 to 25 percent of the one half space charge limited grid current. Non-limiting example upper and lower limits for $I_{grid}$ are shown at 81 and 83, respectively.

The foregoing dimensions and grid voltages represent a specific example structure for a neutron tube ionizer, i.e., the one described with reference to the Chen et al. '410 patent. Based on Child's law (see Eq. 1), a neutron generator tube may obtain longer lifetime according to the present disclosure if, in any combination, a distance between the cathode and the grid, a cathode current (and corresponding electron emission rate) and a voltage applied to the grid result in the combination operating at most about one half (50%) the space charge limit defined by Child's law.

Figure 7:
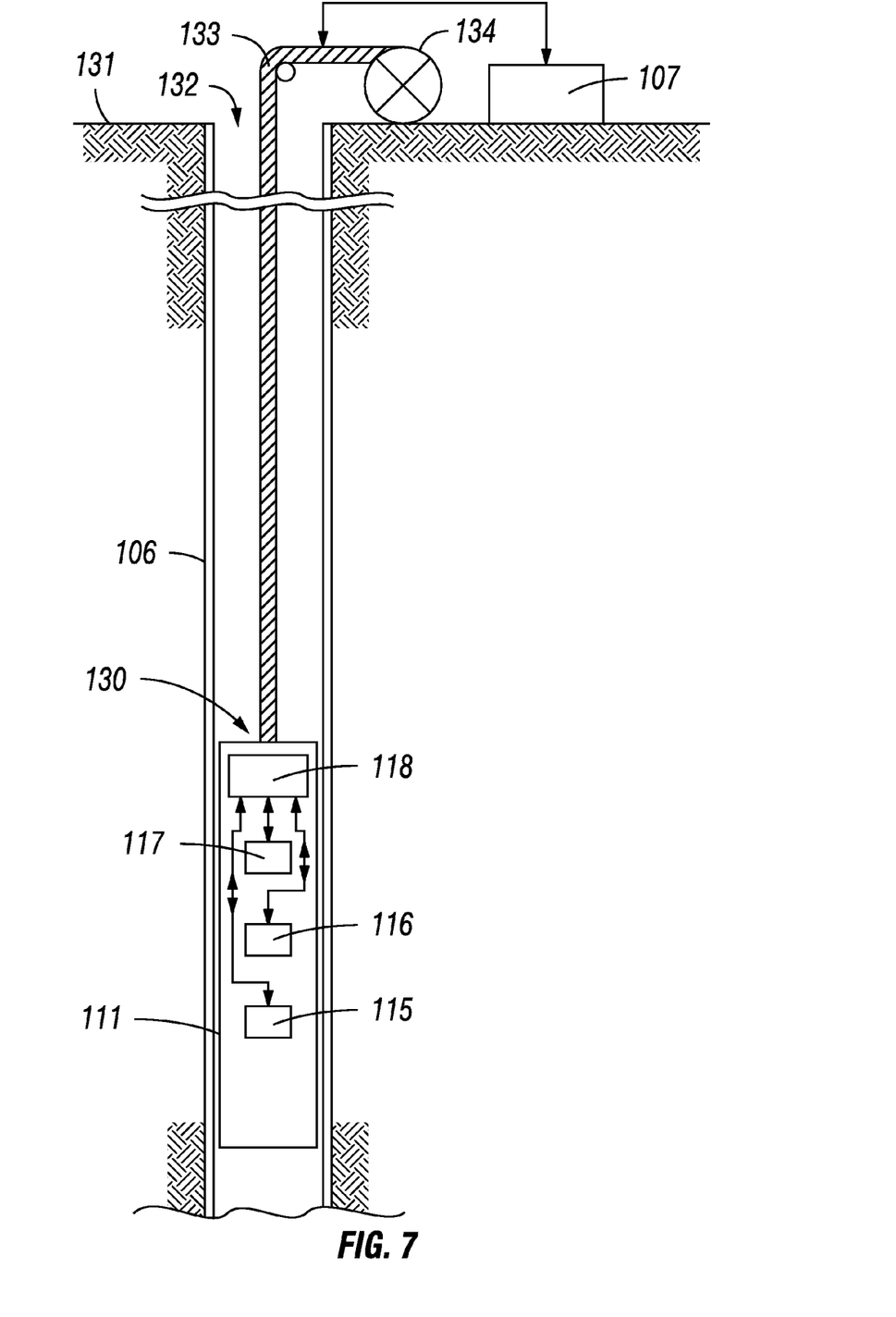
FIG. 7 shows an example wireline conveyed pulsed neutron well logging instrument.

FIG. 7 shows an example apparatus for evaluating subsurface formations 131 traversed by a wellbore 132, which can use a neutron generator tube having an ion generator. The wellbore 132 is typically, but not necessarily filled with a drilling fluid or "drilling mud" which contains finely divided solids in suspension. Deposits of mud solids may deposit on the walls of permeable formations in the wellbore 132 to form mudcake 106. A pulsed neutron logging instrument 130 may be suspended in the wellbore 32 on an armored electrical cable 133, the length of which substantially determines the relative depth of the instrument 130. As is known in the art, this type of instrument can also operate in a well having casing or tubing inserted therein. The length of cable 133 is controlled by suitable means at the surface such as a drum and winch mechanism 134. The depth of the instrument 130 within the wellbore 132 can be measured by encoders in an associated sheave wheel 133, wherein the double-headed arrow represents communication of the depth level information to the surface equipment. Surface equipment, represented at 107, can be of conventional type, and can include a processor subsystem and recorder, and communicates with the all the downhole equipment. It will be understood that processing can be performed downhole and/or at the surface, and that some of the processing may be performed at a remote location. Although the instrument 130 is shown as a single body, the instrument 130 may alternatively comprise separate components such as a cartridge, sonde or skid, and the tool may be combinable with other logging tools. The pulsed neutron well logging instrument 130 may, in a form hereof, be of a general type described for example, in U.S. Pat. No. 5,699,246 incorporated herein by reference. The instrument 130 may include a housing 111 in the shape of a cylindrical sleeve, which is capable, for example, of running in open wellbore, cased wellbore or production tubing. Although not illustrated in FIG. 7, the instrument 130 may also have an eccentering device, for forcing the instrument 130 against the wall of an open wellbore or against wellbore casing. At least one PNG 115 containing a neutron tube, which may include an ionizer may be mounted in the housing 111 with a near-spaced radiation detector 116 and a far-spaced radiation detector 117 mounted longitudinally above the PNG 115, each at a separate axial distance therefrom. One or more further detectors (not shown) can also be provided, it being understood that when the near and far detectors are referenced, use of further detectors can, whenever suitable, be included as well. Also, it can be noted that a single radiation detector could be used. Acquisition, control, and telemetry electronics 118 serves, among other functions, to control the timing of burst cycles of the PNG 115, the timing of detection time gates for the near 116 and far 117 radiation detectors and to telemeter count rate and other data using the cable 133 and surface telemetry circuitry, which can be part of the surface instrumentation 107. The surface processor of surface instrumentation 107 can, for example, receive detected thermal neutron counts, detected epithermal neutron counts and/or gamma ray spectral data from near and far radiation detectors 116 and 117. The signals can be recorded as a "log" representing measured parameters with respect to depth or time on, for example, a recorder in the surface instrumentation 107. The one or more measured parameters may be used to determine one or more properties of the formations from characteristics of the measured radiation. The radiation detectors may include one or more of the following types of radiation detectors, thermal neutron detectors (e.g., $^3$He proportional counters), epithermal neutron detectors and scintillation counters (which may or may not be used in connection with a spectral analyzer).

The PNG which uses a neutron tube with an ionization chamber described above can also be used, for example, in logging-while-drilling ("LWD") equipment. As shown, for example, in FIG. 8, a platform and derrick 210 are positioned over a wellbore 212 that may be formed in the Earth by rotary drilling. A drill string 214 may be suspended within the borehole and may include a drill bit 216 attached thereto and rotated by a rotary table 218 (energized by means not shown) which engages a kelly 220 at the upper end of the drill string 214. The drill string 214 is typically suspended from a hook 222 attached to a traveling block (not shown). The kelly 220 may be connected to the hook 222 through a rotary swivel 224 which permits rotation of the drill string 214 relative to the hook 222. Alternatively, the drill string 214 and drill bit 216 may be rotated from the surface by a "top drive" type of drilling rig.

Figure 8:
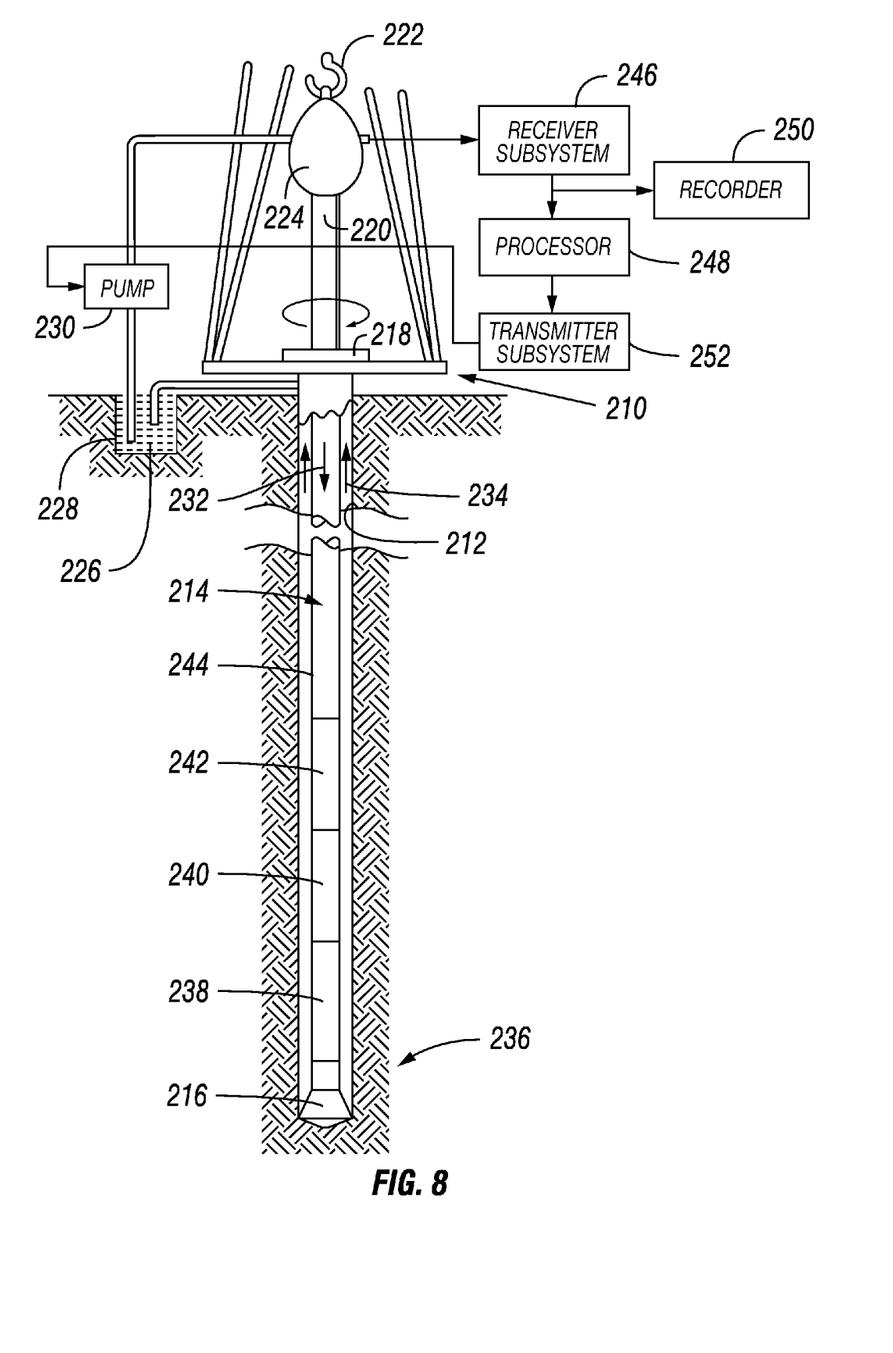
FIG. 8 shows an example logging while drilling ("LWD") pulsed neutron well logging instrument.

Drilling fluid or mud 226 is contained in a mud pit 228 adjacent to the derrick 210. A pump 230 pumps the drilling fluid 226 into the drill string 214 via a port in the swivel 224 to flow downward (as indicated by the flow arrow 232) through the center of the drill string 214. The drilling fluid exits the drill string via ports in the drill bit 216 and then circulates upward in the annular space between the outside of the drill string 214 and the wall of the wellbore 212, as indicated by the flow arrows 234. The drilling fluid 226 thereby lubricates the bit and carries formation cuttings to the surface of the earth. At the surface, the drilling fluid is returned to the mud pit 228 for recirculation. If desired, a directional drilling assembly (not shown) could also be employed.

A bottom hole assembly ("BHA") 236 may be mounted within the drill string 214, preferably near the drill bit 216. The BHA 236 may include subassemblies for making measurements, processing and storing information and for communicating with the Earth's surface. The bottom hole assembly is typically located within several drill collar lengths of the drill bit 216. In the illustrated BHA 236, a stabilizer collar section 238 is shown disposed immediately above the drill bit 216, followed in the upward direction by a drill collar section 240, another stabilizer collar section 242 and another drill collar section 244. This arrangement of drill collar sections and stabilizer collar sections is illustrative only, and other arrangements of components in any implementation of the BHA 236 may be used. The need for or desirability of the stabilizer collars will depend on drilling conditions.

In the arrangement shown in FIG. 8, the components of a downhole pulsed neutron measurement subassembly that may include a PNG with a neutron tube as explained with reference to FIGS. 2 and 8 and may be located in the drill collar section 240 above the stabilizer collar 238. Such components could, if desired, be located closer to or farther from the drill bit 216, such as, for example, in either stabilizer collar section 238 or 242 or the drill collar section 244. The drill collar section 240 may include one or more radiation detectors (not shown in FIG. 8) substantially as explained with reference to FIG. 7.

The BHA 236 may also include a telemetry subassembly (not shown) for data and control communication with the Earth's surface. Such telemetry subassembly may be of any suitable type, e.g., a mud pulse (pressure or acoustic) telemetry system, wired drill pipe, etc., which receives output signals from LWD measuring instruments in the BHA 236 (including the one or more radiation detectors) and transmits encoded signals representative of such outputs to the surface where the signals are detected, decoded in a receiver subsystem 246, and applied to a processor 248 and/or a recorder 250. The processor 248 may comprise, for example, a suitably programmed general or special purpose processor. A surface transmitter subsystem 252 may also be provided for establishing downward communication with the bottom hole assembly.

The BHA 236 can also include conventional acquisition and processing electronics (not shown) comprising a microprocessor system (with associated memory, clock and timing circuitry, and interface circuitry) capable of timing the operation of the accelerator and the data measuring sensors, storing data from the measuring sensors, processing the data and storing the results, and coupling any desired portion of the data to the telemetry components for transmission to the surface. Alternatively, the data may be stored downhole and retrieved at the surface upon removal of the drill string. Power for the LWD instrumentation may be provided by battery or, as known in the art, by a turbine generator disposed in the BHA 236 and powered by the flow of drilling fluid.

A pulsed neutron generator tube using a hot dispenser cathode wherein space charge limits are set in the ion generator using cathode to grid spacing and/or grid voltages as described herein may have longer cathode life than hot (dispenser) cathode-based pulsed neutron generator structures known in the art.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for operating a pulsed neutron generator, comprising an ionizer including an electron emitting cathode and a grid, the cathode and grid disposed in a sealed chamber, the method comprising:

selecting at least one of a cathode electron emission rate, a distance between the cathode and the grid and a potential applied to the grid such that the ion generator operates at most about one-half a space charge limited current for a grid current selected to provide a predetermined amount of neutron production.

2. The method of claim 1 wherein the electron emitting cathode is a heated cathode.

3. The method of claim 1 wherein the electron emitting cathode is an unheated cathode.

4. The method of claim 1 wherein the distance between the cathode and the grid is less than 0.055 inches.

5. The method of claim 1 wherein the potential is less than 200 volts.

6. The method of claim 1 wherein the cathode surface area is at most 12 mm$^2$.

7. A method for pulsed neutron well logging, comprising:
   disposing a pulsed neutron well logging instrument having a pulsed neutron generator and at least one radiation detector axially spaced apart therefrom into a wellbore, the pulsed neutron generator having an ionizer including an electron emitting cathode and a grid, the cathode and grid disposed in a sealed chamber wherein at least one of a cathode electron emission rate, a distance between the cathode and the grid and a potential applied to the grid are selected such that the ion generator operates at most about one-half a space charge limited current for a grid current selected to provide a predetermined amount of neutron production; and
   operating the pulsed neutron generator to produce neutrons to irradiate formations adjacent to the wellbore.

8. The method of claim 7 further comprising determining at least one formation property from characteristics of radiation detected by the at least one radiation detector in response to interaction with the neutrons.

9. The method of claim 7 wherein the electron emitting cathode is a heated cathode.

10. The method of claim 7 wherein the electron emitting cathode is an unheated cathode.

11. The method of claim 7 wherein the distance between the cathode and the grid is less than 0.055 inches.

12. The method of claim 7 wherein the potential is less than 200 volts.

13. The method of claim 7 wherein the cathode surface area is at most 12 mm$^2$.

14. The method of claim 7 further comprising moving the pulsed neutron well logging instrument along an interior of the wellbore and making a record with respect to axial position in the wellbore of an output of at least one radiation detector associated with the pulsed neutron well logging instrument.

15. The method of claim 14 further comprising making a record with respect to the axial position of at least one formation property determined from characteristics of the output of the at least one radiation detector.

16. The method of claim 14 wherein the moving the pulsed neutron well logging instrument comprises changing a length of a cable coupled to the pulsed neutron well logging instrument.

17. The method of claim 14 wherein the moving the pulsed neutron well logging instrument comprises moving a drill string having the pulsed neutron well logging instrument forming a part thereof along the wellbore.

18. The method of claim 17 wherein the moving the drill string is performed during drilling of the wellbore.

* * * * *